United States Patent

Steinkamp et al.

[11] Patent Number: 5,116,382
[45] Date of Patent: May 26, 1992

[54] PROSTHESIS CAPTURE DEVICE

[75] Inventors: Stephen P. Steinkamp, Elizabethtown; Jeffrey C. Batzer, Lancaster, both of Pa.

[73] Assignee: Victory Prosthetic Systems, Inc., Lancaster, Pa.

[21] Appl. No.: 532,918

[22] Filed: Jun. 4, 1990

[51] Int. Cl.⁵ .................................... A61F 2/62
[52] U.S. Cl. ........................ 623/38; 623/27; 403/4; 403/353
[58] Field of Search .................. 623/16, 39, 38, 34, 623/27, 38, 57; 403/319, 358, 4, 353, 407.1

[56] References Cited

U.S. PATENT DOCUMENTS

| | | | |
|---|---|---|---|
| 1,193,969 | 8/1916 | Aunger | 623/57 |
| 1,350,743 | 8/1920 | Skoglund | |
| 2,537,621 | 1/1951 | Busom | 403/407.1 X |
| 2,897,512 | 8/1959 | Sackett | 623/34 |
| 3,400,408 | 9/1968 | Garcia | 623/38 |
| 3,414,908 | 12/1968 | Waggott | 623/38 |
| 3,422,462 | 1/1969 | Finnieston | 623/33 |
| 3,461,464 | 8/1969 | Lindgren | 623/38 |
| 3,538,516 | 10/1967 | Bailey | 623/38 |
| 3,659,294 | 5/1972 | Glabiszewski | 623/33 |
| 4,035,093 | 7/1977 | Redshaw | 403/4 |
| 4,274,165 | 6/1981 | Iuko et al. | 623/57 |
| 4,282,766 | 8/1981 | Huber | 403/353 X |
| 4,283,800 | 8/1918 | Wilson | 623/27 |
| 4,564,365 | 1/1986 | Winer | 623/27 |
| 4,608,054 | 8/1986 | Schroder | 623/27 |

FOREIGN PATENT DOCUMENTS

| | | | |
|---|---|---|---|
| 0325736 | 8/1989 | European Pat. Off. | 403/4 |
| 0308672 | 10/1918 | Fed. Rep. of Germany | 623/27 |
| 1040394 | 10/1953 | France | 623/57 |
| 0414633 | 1/1947 | Italy | 623/27 |
| 0100471 | 5/1916 | United Kingdom | 623/57 |

Primary Examiner—Randall L. Green
Assistant Examiner—David H. Willse
Attorney, Agent, or Firm—Martin Fruitman

[57] ABSTRACT

A prosthetic capture device to interconnect a sleeve which grips a stump of a limb with a prosthesis. The silicone sleeve is constructed with a threaded screw protruding down from the bottom of the sleeve. A spring loaded sliding plate with a keyhole shaped hole, operating in conjunction with a fixed plate with a circular hole, is used to capture the screw head when it is inserted into the prosthesis. An adjustment plate attached to the capture device on the prosthesis has two circular sections which fit into a base plate, and each of the circular sections has a slot into which is set a clamping screw. The base plate is connected to the body of the prosthesis. The base plate can be moved in an elliptical pattern relative to the prosthesis as the clamping screws slide in the slots.

7 Claims, 3 Drawing Sheets

PROSTHESIS CAPTURE DEVICE

SUMMARY OF THE INVENTION

This invention deals generally with prosthetics and more specifically with a capture device to attach an artifical limb to the stump of the natural limb.

One method of securing a prosthesis to a user uses a silicone suction suspension system, a pliable silicone sleeve which grips the stump of a limb, around which is fitted and to which is attached a socket assembly which includes a relatively rigid shell-like socket. The socket assembly has attached to it a pylon which connects the socket assembly to an artificial foot.

The means of attaching the socket assembly to the sleeve is always built into the closed end of the socket near the point at which the pylon is connected, because that is the only location available on the silicone sleeve for the part of the attachment system which must be mounted on the sleeve.

The most typical systems available for attaching the sleeve to the socket include either a bolt with a "D" shaped ring at the bolt head or plunger with multiple barbs. Either one of these fittings protrudes from the bottom of the silicone sleeve. The fittings are threded into a plate cast into the bottom of the sleeve, so that their protrusion from the sleeve, and therefore the sleeve's spacing from the socket, can be adjusted by merely turning the fitting into or out of the plate into which it is threaded.

When the "D" bolt is used, the capture device on the socket is usually a straight movable pin which pierces the "D" and thus prevents the socket from separating from the sleeve. Pulling the pin out permits the parts to be separated or installed because the pin is then pulled clear of the "D" ring.

For the barbed type connector, a spring loaded pin is used, and the nature of the shape of the plunger is such that installation of the sleeve into the socket does not require manual operation of the spring loaded pin, since the wedge shape of the barbs permit automatic insertion. Nevertheless, for detachment of the sleeve from the socket, pulling the pin free of the plunger is still required.

However, both of these attachment systems have been found to have deficiencies. For instance, the "D" ring can only be adjusted in increments of approximately one-half turn of the thread, since the pin will not pierce it if it is oriented in the same plane as the motion of the pin.

The barb plunger has another problem in that it can tighten up during use. If activity of the user forces it temporarily further into the socket, it may grip an additional barb and remain tightly locked unless manually reset.

Furthermore, both of these existing connection systems require excessive height for their structure, and this height limits their use by some amputees because there is simply not enough height to use them with certain pylon systems.

The present invention overcomes all of these limitations by furnishing a low profile, positive retention, capture device which does not become tighter with use.

The actual capture mechanism is a sliding plate with a keyhole shaped slot within it. This keyhole plate slides within a recess within a base plate which has a central circular hole, and the keyhole plate is retained in place by a cover plate which also has a central hole which matches the one in the base plate. The keyhole plate can be spring located so that only its narrow slot is normally aligned with the holes in the base and cover plates, but pushing an activating rod moves the circular part of the keyhole into alignment with the holes in the base and cover plates. This provides a circular clearance hole through the entire assembly as long as the activating rod is held against the force of the spring.

In that condition, the screw head protruding from the silicone sleeve on the natural limb can be inserted through the clearance hole formed in the capture assembly, and when the activating rod is released, the slot moves to replace the circular portion of the keyhole, and it traps the screw head in the hole in the base plate.

In order to release the screw head from the capture assembly, it is only necessary to push the activating rod in again, and remove the screw head from the capture assembly.

The present invention also includes a means to adjust the alignment of the pylon which is attached to the capture device, and this adjustment system adds very little to the height of the entire assembly. To accomplish this, a single adjustment plate is attached to the bottom of the base plate, the side of the base plate opposite from the keyhole plate. This adjustment plate includes conventional tapped holes which will accept screws to hold the pylon which connects an artificial foot to the adjustment plate, but the means for holding the adjustment plate against the base plate includes the adjustment means.

The adjustment plate has two large circular through holes within it, and each of these holes has stepped sides so that it has a smaller diameter at the surface which contacts the base plate. Circular step sided inserts are located within each of the large circular holes and match their configurations, so that the inserts may rotate within the holes. Each insert then has a step sided slot within it, and like the step sides of the circular holes, the smaller openings of the slots are adjacent to the base plate.

Step sided slide fittings are located within and match each of the slots, and the slide fittings have threaded holes through their centers. The adjustment plate is held against the base plate by clamping screws which go through the cover plate and the base plate and are threaded into the holes in the slide fittings. Since the heads of the clamping screws are located against the cover plate, the heads are acessible from inside the socket.

With this configuration and because of the step sides of the various holes, the slide fittings are held against the base plate by the screws, the slide fittings hold the circular inserts against the base plate, and the circular inserts hold the adjustment plate against the base plate. When the clamping screws are tightened, the entire adjustment assembly is held tightly against the base plate, but when the clamping screws are loose, the adjustment plate's position upon the base plate can be varied.

When the center of the large circular holes are located on a diameter of the adjustment plate and because of the slots within the inserts, the adjustment plate can be moved and located anywhere within the limits of an elliptical adjustment pattern on the base plate. Such an adjustment pattern permits the pylon axis to be adjusted relative to the limb of the user, and although such an adjustment is normally done only at the fitting of the artificial limb, the ease of the adjustment makes it possible to do so quickly and to make small adjustments for added comfort at a later time.

The present invention is therefore able to furnish both a reliable capture device and a convenient adjustment system within an extremely low profile. It requires a total of only three relatively thin plates to accomplish both functions, and thereby permits a greater variety of prosthetic components to be worn by a greater number of people who need them.

DETAILED DESCRIPTION OF THE INVENTION

Figure 1:
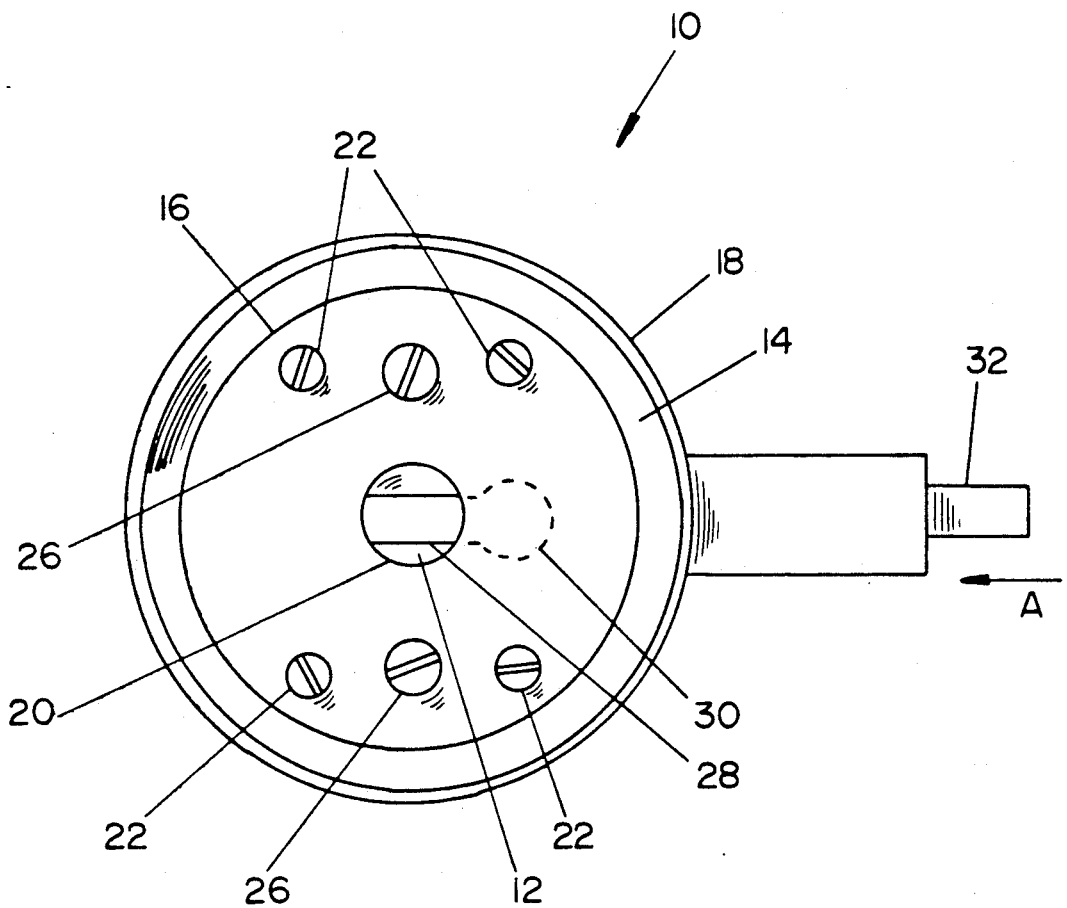
FIG. 1 is a top plan view of the preferred embodiment of the invention.

The preferred embodiment of the invention is shown in FIG. 1 in a top plan view, that is, the view looking at the top of capture device 10 as it would be seen when looking into the socket of the prosthesis. This is the view which the user sees as he about to place his natural limb, which would be in a silicone sleeve, into the prosthesis socket.

Capture device 10 would be cast into the prosthesis socket (not shown) which is shaped somewhat as a truncated cone. Capture device 10 is located at the smaller end of the socket and closes off that end. The larger end of the socket is open, and it is that open end into which the user inserts his limb which is covered with the silicone sleeve. The silicone sleeve haas the head end of a simple threaded screw or a rod with a larger diameter end, similar to the appearance of a screw with a head (not shown), protruding from the lower end of the sleeve.

Capture device 10 is constructed with keyhole plate 12 sandwiched between base plate 14 and cover plate 16. Base plate 14 includes wall 18 protruding upward from its circular perimeter so that it forms a cup-like structure. Cover plate 16 sits in the bottom of this cup. Wall 18 serves no fuction in the capture mechanism, but is used to secure the capture device to the socket, in that it is cast into the socket shell to form the bottom end of the socket.

Cover plate 16, which includes center hole 20, is attached to base plate 14 with several screws 22 which go through clearance holes in cover plate 16 and into threaded holes in base plate 14.

Screws 26 are used in the adjustment function of capture device 10 which will be explained below in regard to FIG. 3.

Keyhole plate 12, which is held between cover plate 16 and base plate 14, can be seen in FIG. 1 only through center hole 20 in cover plate 16, and keyhole plate 12 is shown in its normal position, when it holds onto the securing means protruding from the socket, with only the slotted portion 28 of its keyhole shaped opening 30 visible through hole 20.

In order to insert a screw head or other securing means (not shown) protruding from a silicone sleeve into capture device 10, rod 32 is moved in direction A, which displaces keyhole plate 12 in the same direction and therefore aligns the circular portion of keyhole slot 30 with hole 20. The securing means can then be inserted through cover plate 16 and keyhole plate 12 and into central hole 40 (FIG. 2) in base plate 14. When rod 32 is released, it is spring loaded to move back to the position shown in FIG. 1, and slotted portion 28 of keyhole opening 30 holds the securing means which had been inserted within capture device 10.

Figure 2:
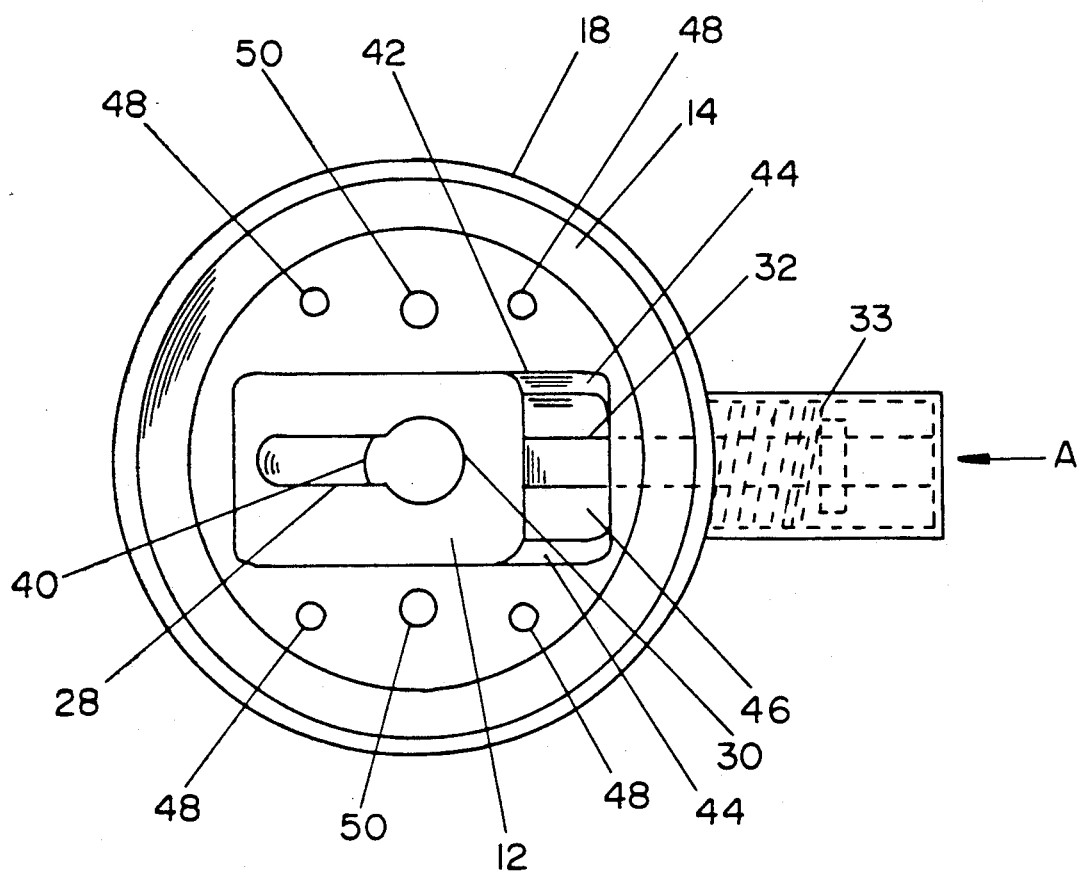
FIG. 2 is a top plan view of the preferred embodiment of the invention with the cover plate removed.

This action can better appreciated by referring to FIG. 2, which is the same view as FIG. 1, except cover plate 16 has been removed to view the mechanism of capture device 10, and keyhole plate 12 positioned as it would be if rod 32 were moved in direction A to its full extent. FIG. 2 also shows spring 33 with invisible lines. This is the spring which holds rod 32 in its normal position and against which rod 32 is operated.

In FIG. 2, keyhole plate 12 can be seen in its entirety. Keyhole plate 12 is moved fully to the left of slot 42 so that the circular portion of hole 30 is aligned with circular central hole 40 of base plate 14. Slot 42 includes lips 44 which support keyhole plate 12, and slot 42 also has a deeper region 46 which permits rod 32 to be located in a plane below the bottom of keyhole plate 12.

FIG. 2 also shows threaded holes 48 in base plate 14 which accept screws 22 (FIG. 1) to hold cover plate 16 onto base plate 14 so that it can act as a retaining means to hold keyhole plate 12 within slot 42. Clearance holes 50 in base plate 14 can also be seen. They accommodate screws 26 (FIG. 1) which pass through base plate 14 and function clamp adjustment 52 to base plate 14, as can be better understood by reference to FIG. 3.

Figure 3:
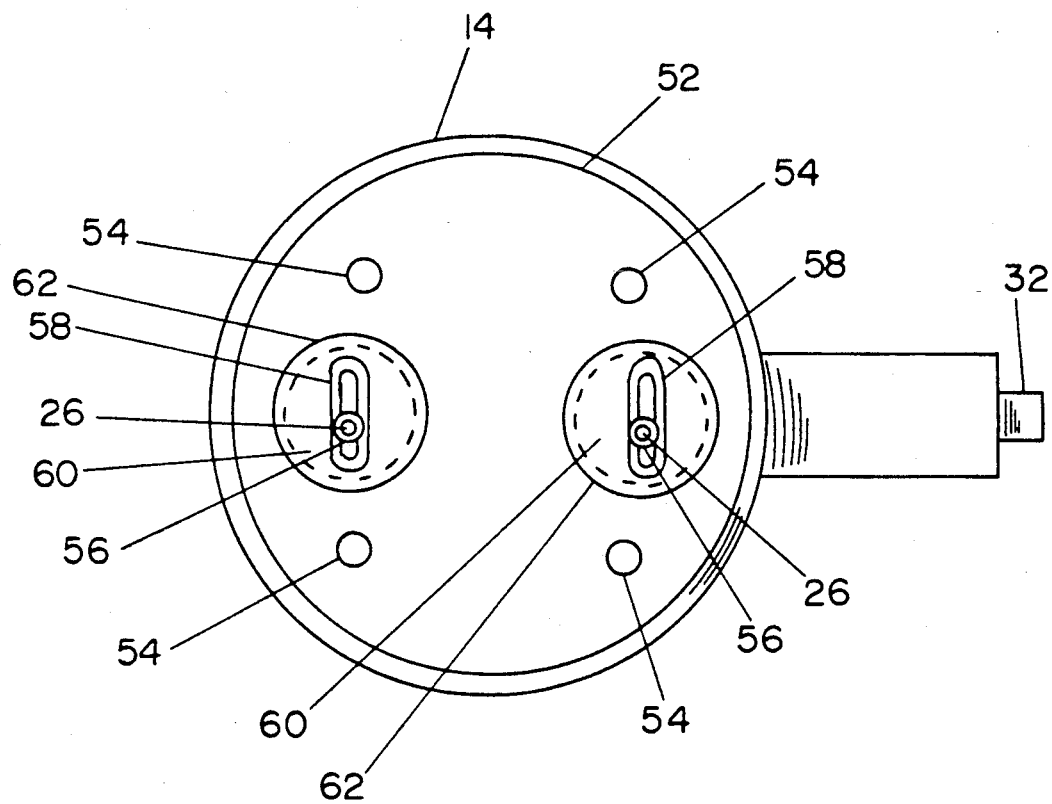
FIG. 3 is a bottom plan view of the preferred embodiment of the invention showing the adjustment plate.

FIG. 3 is a bottom plan view of the preferred embodiment of the invention. This view would not normally be available while capture device 10 is in use, because adjustment plate 52 would be covered by the prosthesis. The pylon of the prosthesis would be attached to adjustment plate 52 by use of threaded holes 54, which could be in any desirable pattern and could also be of a greater or lesser number.

The adjustment system pictured in FIG. 3 involves adjustment screws 26 (FIG. 1) which extend through entire capture device 10 and thread into slide fitting 56 to hold adjustment plate 52 against base plate 14. Slide fittings 56 are constructed with step sides, the smaller portion of which fits into the narrow portion of step sided slots 58 which are formed in circular inserts 60. Circular inserts 60 also have step sides on their outer edges, with the smaller diameters located nearest base plate 14, and the edges match with the sides of circular holes 62 in adjustment plate 52. Circular holes 62 also have step sides with the smaller diameters nearer to base plate 14.

This construction permits slide fittings 56, which are held by screws 26, to hold circular inserts 60 against the step sides of holes 62, and thereby hold adjustment plate 52 against base plate 14. With this clamping action it is apparent that, when screws 26 are loose so that slide fittings 56 permit movement, adjustment plate 52 can be varied in its location.

Although slide fittings 56 are fixed in their locations by screws 26, circular inserts 60 can be moved relative to slide fittings 56, and that permits adjustment plate 52 to move relative to base plate 14. The actual variation in the position of adjustment plate 52 covers an area whose perimeter is an ellipse, when the holes in base plate 14 through which screws 26 penetrate are on a diameter of base plate 14 equally spaced from the center of base plate 14.

. The structure shown here for the preferred embodiment of the invention is particularly advantageous because it has a very small height dimension, but still permits all the adjustment which is normally required for proper fit of a prosthesis. Moreover, it enables the user to easily capture and release the securing means on the silicone suction sleeve, and it furnishes a capture device which does not inadvertently tighten to make the user uncomfortable.

It is to be understood that the form of this invention as shown is merely a preferred embodiment. Various changes may be made in the function an arrangement of parts; equivalent means may be substituted for those illustrated and described; and certain features may be used independently from others without departing from the spirit and scope of the invention as defined in the following claims.

For example, different locations could be used for the various screws, or for the centers of the circular inserts of FIG. 3, and securing means other than a screw protruding from the sleeve could be captured by the keyhole construction. Moreover, retaining means other than cover plate 16 could be used to hold keyhole plate 12 in place, for instance, tabs extending over the edges of slot 42.

What is claimed as new and for which Letters Patent of the United States are desired to be secured is:

1. A capture device to attach a prosthesis to a securing means protruding from a sleeve on a natural limb of an amputee comprising:
    a base plate with a first hole which is large enough to accept a securing means protruding from a sleeve on a natural limb of a user and with a slot located so that the first hole is within the slot:
    a keyhole plate located within the slot in the base plate and including a keyhole shaped through hole which includes a circular portion large enough to clear the securing means and an attached slotted portion which is small enough to prevent the securing means from passing through the slotted portion, the keyhole plate being sized and located within the slot in the base plate so that, when the keyhole plate is moved toward one end of the slot in the base plate the circular portion of the keyhole shaped hole is aligned with the first hole in the base plate, and when the keyhole plate is moved toward the other end of the slot in the base plate, the slotted portion of the keyhole shaped hole is aligned with the first hole in the base plate;
    an actuator means for imparting motion to the keyhole plate and extending away from the keyhole plate and the base plate so that the actuator means can be operated by a user in order to move the keyhole plate within the slot in the base plate;
    retaining means attached to the base plate and holding the keyhole plate within the slot in the base plate, the retaining means having an opening aligned with the first hole and at least large enough for the securing means protruding from the sleeve to pass through the opening and the retaining means is a cover plate which is attached to the base plate by at least one screw so that each screw penetrates the cover plate and is fitted into a threaded hole within the base plate; and
    attachment means for attaching components to the capture device.

2. The capture device of claim 1 further including a spring means acting upon the keyhole plate and forcing the keyhole plate into a position which locates the slotted portion of the keyhole shaped hole so that it is aligned with the first hole in the base plate.

3. The capture device of claim 1 further including a wall attached to the perimeter of the base plate and extending transversely to the surface of the base plate to form a cup-like structure with the base plate.

4. The capture device of claim 1 wherein the attachment means is an adjustment means comprising:
    an adjustment plate, in contact with the base plate surface opposite from the surface to which the retaining means is attached, the adjustment plate having two circular through holes with step sides so that the circular holes each have a larger diameter at one surface of the adjustment plate and a smaller diameter at the other surface of the adjustment plate which is the surface nearest to the base plate;
    two circular inserts, each inserted into and with sides matching each of the circular holes, each insert having a through slot within the insert, with each slot having step sides so that the slot has two different widths, with the narrower width being adjacent to the base plate;
    two fittings, each inserted into and with sides matching each of the slots in the inserts, the fittings being smaller than the length of the slots and being capable of sliding within the slots, with each of the fittings having a threaded hole within it; and
    two screws, the head of which are on the side of the base plate most remote from the adjustment plate, the screws passing through holes in the base plate and threading into the holes within the fittings, so that the screws hold the fittings, inserts and adjustment plate against the base plate.

5. The adjustment means of claim 4 wherein the screws are located on a diameter of a circular base plate and are equally spaced from the center of the base plate.

6. An adjustment means for a prosthesis comprising:
    a base plate attached to a sleeve which is adapted to grip a natural limb of an amputee;
    an adjustment plate, contact with the base plate surface most remote from the sleeve, the adjustment plate having two circular through holes with step sides so that the circular holes each have a larger diameter at one surface of the adjustment plate and a smaller diameter at the other surface of the adjustment plate which is the surface nearest to the base plate;
    two circular inserts, each inserted into and with sides matching each of the circular holes, each insert having a through slot within the insert, with each slot having step sides so that the slot has two different widths, with the narrower width being adjacent to the base plate;
    two fittings, each inserted into and with sides matching each of the slots in the inserts, the fittings being smaller than the length of the slots and being capable of sliding within the slots, with each of the fittings have a threaded hole within it;
    two screws, the heads of which are on the side of the base plate most remote from the adjustment plate, the screws passing through holes in the base plate and threading into the holes within the fittings, so that the screws hold the fittings, inserts and adjustment plate against the base plate; and
    attachment means on the adjustment plate to hold components onto the adjustment plate.

7. The adjustment means of claim 6 wherein the screws are located on a diameter of a circular base plate and are equally spaced from the center of the base plate.

* * * * *